(12) United States Patent
Van Bohemen et al.

(10) Patent No.: US 12,414,725 B2
(45) Date of Patent: Sep. 16, 2025

(54) METHOD AND APPARATUS FOR DETECTING CHANGES IN BLOOD FLOW IN THE HEAD OF A SUBJECT

(71) Applicant: Nuroflux Pty Ltd, Mascot (AU)

(72) Inventors: Samuel Jacobus Van Bohemen, Sydney (AU); Philip Boughton, Sydney (AU); Andre Kyme, Sydney (AU)

(73) Assignee: NUROFLUX PTY LTD, Mascot (AU)

( * ) Notice: Subject to any disclaimer, the term of this patent is extended or adjusted under 35 U.S.C. 154(b) by 707 days.

(21) Appl. No.: 17/771,581

(22) PCT Filed: Aug. 27, 2020

(86) PCT No.: PCT/AU2020/050896
§ 371 (c)(1),
(2) Date: Apr. 25, 2022

(87) PCT Pub. No.: WO2021/077154
PCT Pub. Date: Apr. 29, 2021

(65) Prior Publication Data
US 2022/0409117 A1 Dec. 29, 2022

(30) Foreign Application Priority Data
Oct. 25, 2019 (AU) ................. 2019904029

(51) Int. Cl.
*A61B 5/026* (2006.01)
*A61B 5/00* (2006.01)
*A61B 5/346* (2021.01)
(52) U.S. Cl.
CPC .............. *A61B 5/346* (2021.01); *A61B 5/026* (2013.01); *A61B 5/4064* (2013.01);
(Continued)

(58) Field of Classification Search
CPC ....... A61B 5/346; A61B 5/026; A61B 5/4064; A61B 5/4842; A61B 5/6803;
(Continued)

(56) References Cited

U.S. PATENT DOCUMENTS 9,579,060 B1 * 2/2017 Lisy ..................... A61B 5/4803
9,888,858 B2 * 2/2018 Farrugia ........... A61M 16/0683
(Continued)

FOREIGN PATENT DOCUMENTS

WO  WO 2016/021845   2/2016
WO  WO 2018/116308   6/2018

OTHER PUBLICATIONS

International Search Report issued in PCT International Patent Application No. PCT/AU2020/050896, 3 pp.

*Primary Examiner* — Eugene T Wu
(74) *Attorney, Agent, or Firm* — NIXON & VANDERHYE P.C.

(57) ABSTRACT

A method of detecting changes in blood flow in a head of a subject includes measuring a value of a parameter of a cardiac bioelectrical signal at a scalp area of the subject relative to a reference cardiac bioelectrical signal. The method also includes comparing the value of the measured parameter with a predetermined value of the parameter to determine any change in blood flow in the head of the subject. The determined change can be used to detect changes in perfusion in the brain of a subject for example, as a result of anti-coagulation medication used to dissolve a clot in a blood vessel of the brain of a subject who has experienced ischaemic stroke.

10 Claims, 6 Drawing Sheets

(52) U.S. Cl.
CPC .......... *A61B 5/4842* (2013.01); *A61B 5/6803* (2013.01); *A61B 5/6823* (2013.01); *A61B 5/7275* (2013.01)

(58) Field of Classification Search
CPC . A61B 5/6823; A61B 5/7275; A61B 5/14551; A61B 5/4848; A61B 2562/0219; A61B 2562/0271; A61B 5/318; A61B 5/369; A61B 5/0245; A61B 5/372; A61B 5/0006; A61B 5/7271
See application file for complete search history.

(56) References Cited

U.S. PATENT DOCUMENTS

| | | | |
|---|---|---|---|
| 2009/0227881 A1* | 9/2009 | Reichman | A61B 5/6814 600/506 |
| 2011/0196245 A1* | 8/2011 | Poupko | A61B 5/02028 600/506 |
| 2015/0257673 A1 | 9/2015 | Lawrence et al. | |

* cited by examiner

Figure 2. EMS pads placed on upper back. OpenBCI EEG headset recording EMS signal (Top).

Recording of EMS signal using OpenBCI EEG headset (right).

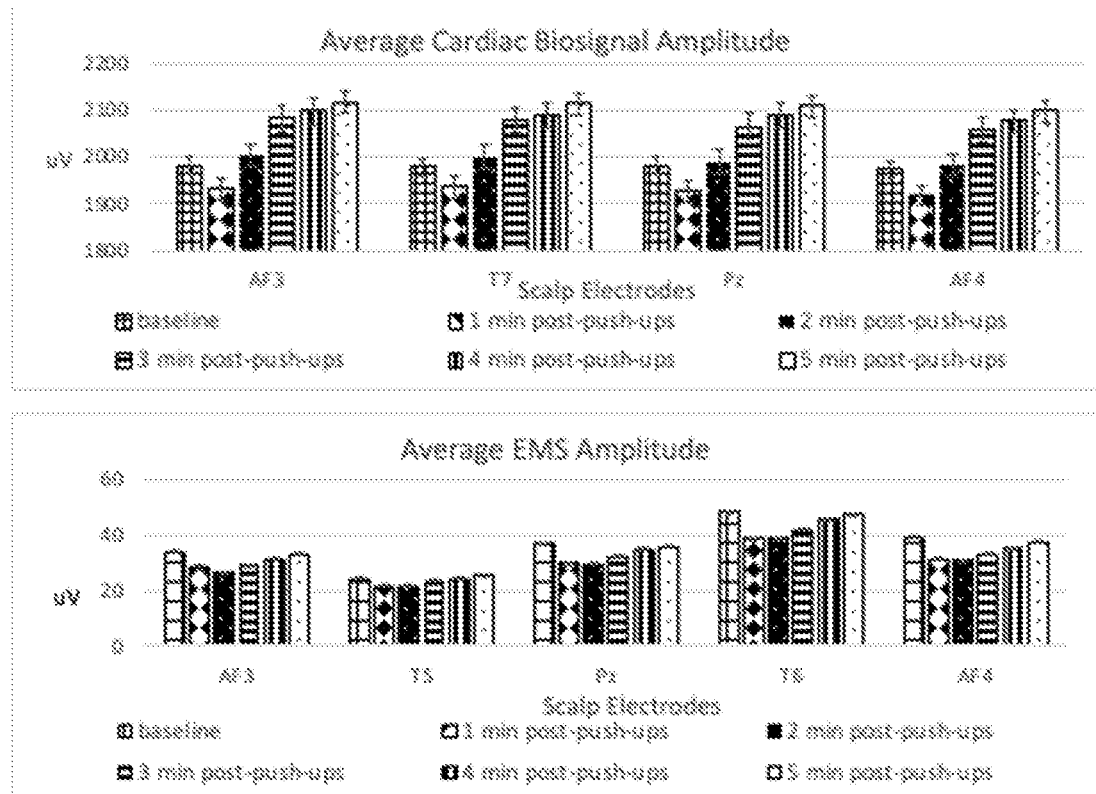
Figure 3. Average cardiac biosignal amplitude before and after anaerobic exercise (Top). Average EMS amplitude before and after anaerobic exercise (bottom). Error bars = standard error of mean
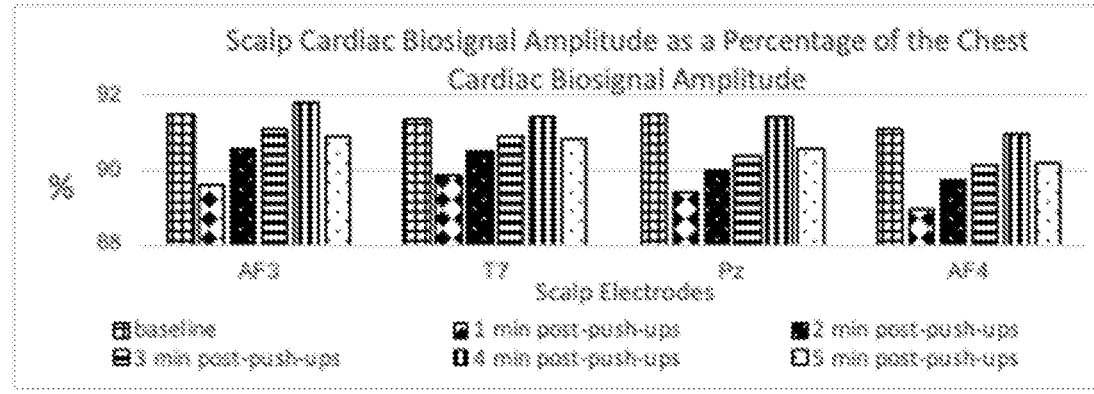
Figure 4. Scalp cardiac biosignal amplitude as a percentage of the chest cardiac biosignal amplitude before and after anaerobic exercise

METHOD AND APPARATUS FOR DETECTING CHANGES IN BLOOD FLOW IN THE HEAD OF A SUBJECT

This application is the U.S. national phase of International Application No. PCT/AU2020/050896 filed Aug. 27, 2020 which designated the U.S. and claims priority to Australian Patent Application No. 2019904029 filed Oct. 25, 2019, the entire contents of each of which are hereby incorporated by reference.

FIELD OF THE INVENTION

The present invention relates to apparatus and method for detecting changes in blood flow in the head of a subject.

The invention has been developed primarily for use monitoring patients who are undergoing or are likely to undergo changes in perfusion in their head and will be described hereinafter with reference to this application. However, it will be appreciated that the invention is not limited to this particular field of use.

BACKGROUND OF THE INVENTION

Stroke is caused by a sudden interruption in the blood supply in the brain. In ischaemic stroke, there is an obstruction in an artery in the brain which prevents blood from accessing a part of the brain.

CT and/or MRI scans are the most common method to assess blood perfusion in the brain in stroke patients to view blood perfusion in the brain.

CT or MRI scans can detect the presence or relative absence of blood in an area of the body and therefore, a blockage (in the case of ischaemic stroke) or a burst blood vessel (in the case of haemorrhagic stroke).

Such scans are also taken to monitor the blood vessels and therefore, blood perfusion in the brain. In the case of ischaemic stroke it can be used during therapy to evaluate the effect of anticoagulant medication delivered to a brain region in dissolving the clot.

However, there are several limitations of these methods. The patient needs to be scanned by a CT or MRI machine under certain conditions. CT and MRI machines are expensive and usually, limited in number. They tend to be bulky.

They also do not provide continuous real-time monitoring of blood perfusion in the brain.

The present invention seeks to provide a solution, which will overcome or substantially ameliorate at least some of the deficiencies of the prior art, or to at least provide an alternative.

It is to be understood that, if any prior art information is referred to herein, such reference does not constitute an admission that the information forms part of the common general knowledge in the art, in Australia or any other country.

SUMMARY OF THE INVENTION

In an aspect of the present disclosure, there is provided a method of detecting changes in blood flow in a head of a subject comprising:
measuring a value of a parameter of a cardiac bioelectrical signal at a scalp area of the subject relative to a reference cardiac bioelectrical signal;
comparing the value of the measured parameter with a predetermined value of the parameter to determine any change in blood flow in the head of the subject.

The reference cardiac bioelectrical signal may be received by a reference electrode located adjacent a heart of the subject.

The method may further include:
measuring a value of the parameter of a cardiac bioelectrical signal at a chest area of the subject relative to the reference cardiac bioelectrical signal;
calculating a ratio of the parameter of the measured cardiac bioelectrical signal at the scalp area of the subject to the parameter of a cardiac bioelectrical signal at the chest area of the subject.

The method may further include comparing the ratio to a predetermined ratio that is indicative of a state of unimpaired blood flow.

The method may further include comparing the ratio to a predetermined ratio that is indicative of a state of impaired blood flow.

The cardiac bioelectrical signal may be an ECG measurement taken at a chest area adjacent the heart of the subject or across a chest area of the subject.

The cardiac bioelectrical signal may be represented by a voltage vs. time graph.

The parameter may be an average peak amplitude of the voltage vs. time graph.

The parameter may be an average peak amplitude of a voltage vs. time graph that is indicative of the measured cardiac bioelectrical signal.

In another aspect, there is provided a headgear apparatus for detecting changes in blood flow in a head of a subject, comprising:
a reference electrode locatable on a chest area adjacent a heart of the subject, in use;
a first electrode locatable on a scalp area of the subject, in use;
a headgear connected to each of the reference electrode and the first electrode, the headgear comprising:
a processing unit configured to measure a value of a parameter of a cardiac bioelectrical signal at a scalp area of the subject relative to a reference cardiac bioelectrical signal and transmit the value of the parameter of that cardiac bioelectrical signal to a computer that is configured to determine a change in blood flow in the head of the subject.

The headgear apparatus may further comprise a second electrode configured to be located at a chest area of the subject, in use, and configured to receive a cardiac bioelectrical signal adjacent the heart, in use.

The processing unit may comprise a brain-computer interface configured to process the cardiac bioelectrical signals received from the electrodes and transmit an indication of the cardiac bioelectrical signals to a receiver.

One or more of the reference electrode, the first electrode and the second electrode may be a wireless electrode.

In yet another aspect there is provided a system for detecting changes in blood flow in a head of a subject, comprising:
a reference electrode locatable at a chest area of the subject;
a first electrode locatable on a scalp area of the subject, the first electrode configured to receive a bioelectrical signal relative to the reference electrode;
a second electrode locatable at a chest area of the subject, in use, and configured to receive a cardiac bioelectrical signal adjacent the heart relative to the reference electrode;
a headgear connected to each of the reference electrode and the first electrode, the headgear comprising:

a processing unit configured to measure a value of a parameter of a cardiac bioelectrical signal received at the scalp area of the subject relative to a reference cardiac bioelectrical signal received at the chest area of the subject and transmit the value of the parameter of that cardiac bioelectrical signal to a computer that is configured to determine a change in blood flow in the head of the subject.

The processing unit may be a brain-computer interface.

The system may further comprise a receiver to receive the transmitted cardiac bioelectrical signal. The receiver may be a wireless receiver.

One or more of the reference electrode, the first electrode and the second electrode may be a wireless electrode.

In yet another aspect, there is provided a method for detecting a change in blood flow in a head of a subject, comprising:

providing a headgear apparatus;
positioning the reference electrode on a chest area adjacent a heart of the subject;
positioning the first electrode on a scalp area of the subject;
positioning the second electrode on a chest area of the subject;
acquiring a reference cardiac bioelectrical signal;
acquiring a cardiac bioelectrical signal at a scalp area of the subject;
transmitting the acquired reference cardiac bioelectrical signal and the acquired cardiac bioelectrical signal at a scalp area of the subject to a processor that is configured to determine a change in blood flow in the head of the subject.

The processor may be configured to determine a change in blood flow in the head of the subject in accordance with the method of detecting changes in blood flow in the head of the subject.

This invention may also be said broadly to consist in the parts, elements and features referred to or indicated in the specification of the application, individually or collectively, and any or all combinations of any two or more of said parts, elements or features, and where specific integers are mentioned herein which have known equivalents in the art to which this invention relates, such known equivalents are deemed to be incorporated herein as if individually set forth.

Other aspects of the invention are also disclosed.

BRIEF DESCRIPTION OF THE DRAWINGS

Notwithstanding any other forms which may fall within the scope of the present invention, embodiments of the invention will now be described, by way of example only, with reference to the accompanying drawings in which:

FIG. 3 shows a chart showing average cardiac biosignal amplitude before and after anaerobic exercise and average amplitude before and after anaerobic exercise.

FIG. 4 is a graph of scalp cardiac biosignal amplitude as a percentage of the chest cardiac biosignal amplitude before and after anaerobic exercise.

DESCRIPTION OF EMBODIMENTS

The heart generates the largest electrical signal in the body. Blood is one of the most electrically conductive components in the body, thus providing a major pathway for electrical signal propagation. The applicant has found that reduced cerebral blood flow (CBF) or blood flow through the head of a subject will decrease this propagation and thus, reduce the amplitude of extra-cerebral electrical signals sensed in a head area such as across the scalp of a subject. The extra-cerebral electrical signal can be a cardiac bioelectrical signal or bioelectrical signals generated by the heart of a subject. The extra-cerebral bioelectrical signal can be another bioelectrical signal. The extra-cerebral bioelectrical signal can be the result of an artificially generated stimulation such as an artificially generated electrical muscle stimulation.

Figure 1:
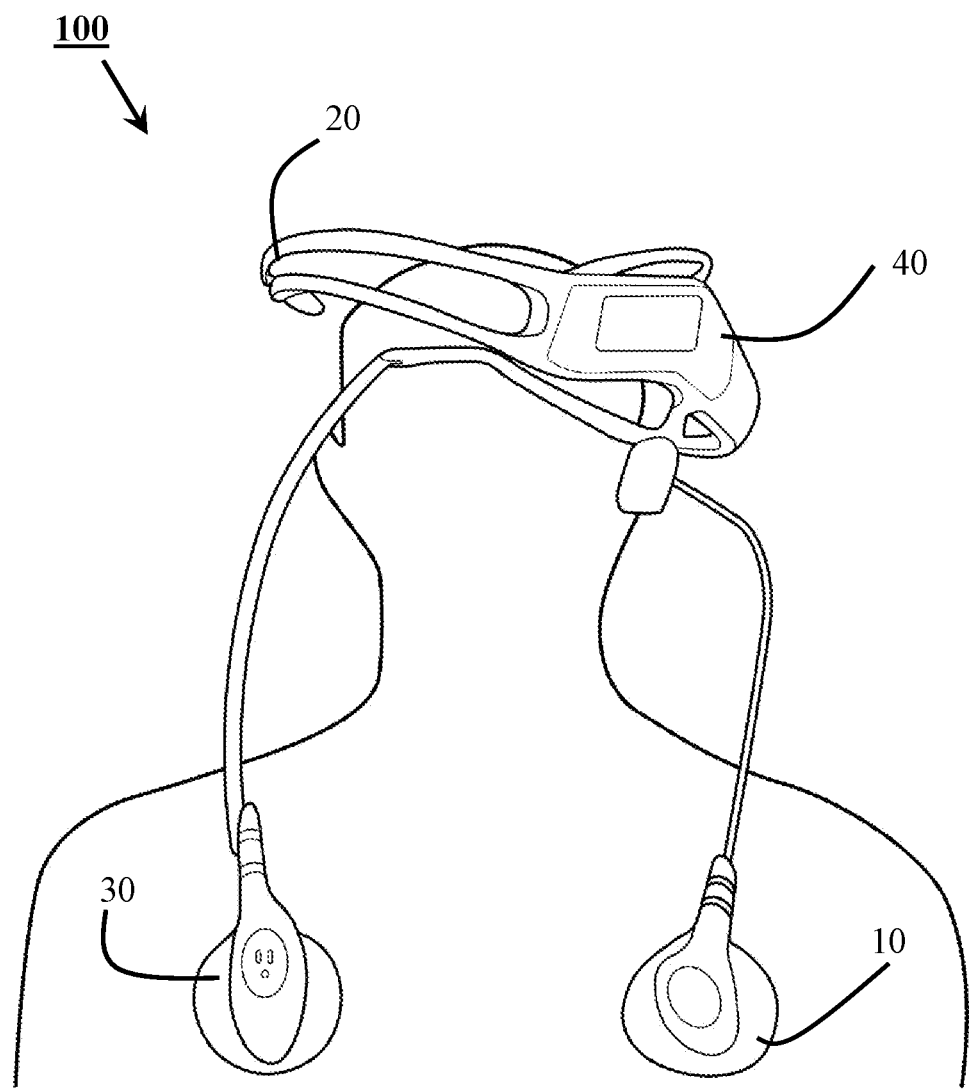
FIG. 1 is a schematic of a headgear apparatus in accordance with an embodiment of the present invention.

FIG. 1 shows an example of a headgear apparatus 100 which can be used to detect changes in blood flow in the head of the subject. In this embodiment, the extra-cerebral bioelectrical signal is a cardiac bioelectrical signal. It is envisaged that in other embodiments, other types of extra-cerebral bioelectrical signals can be used. The headgear apparatus comprises an EEG headset configured to record EEG signals and scalp electrodes operatively coupled with the EEG headset and configured to receive and record bioelectrical signals such as cerebral and extra-cerebral bioelectrical signals.

The headgear apparatus senses the cardiac bioelectrical signal adjacent the heart (e.g. at a chest area of the subject) and adjacent the head (e.g. at a scalp of the subject). This information is sent to a processing unit in the headgear 40 which then transmits the information to a receiver. The receiver sends the information to a computer which includes a processor. The processor can process the information by implementing algorithms to determine any change in blood flow in the head of the subject. The computer can be remote to the headgear apparatus or be part of the headgear apparatus. The processor in the computer can then display the received signals and/or indications of the determined change in blood flow on a display.

As shown in FIG. 1, in use, the reference electrode 10 is located on the left-hand side of the patient's chest (adjacent the heart). A first electrode or first recording electrode 20 is located at a scalp area of the subject. The first electrode 20 can be located at any position on the scalp area of the subject. For example, the first electrode can be located on the scalp area in a position defined by the international 10-20 system for the application of scalp electrodes in the context of an EEG examination.

The first electrode 20 senses the cardiac bioelectrical signal at a head area or the scalp of the subject relative to the reference signal sensed by the reference electrode 10. The applicant has found that by placing the reference electrode 10 adjacent the heart of the patient e.g. at a chest area of the patient, and recording the electrical activity at a scalp area of the patient with the first electrode 20, that the component of electrical activity at the scalp that is related to the heart (cardiac bioelectrical activity at a scalp area of the subject) is pronounced or can be detected easily.

As shown in FIG. 1, a second recording electrode 30 is placed on a chest area of the patient near the reference electrode 10. The applicant has found that the signal recorded by this second electrode relative to the reference signal indicates the bioelectrical activity closest to the heart of the subject while the heart pumps blood.

Figure 6:
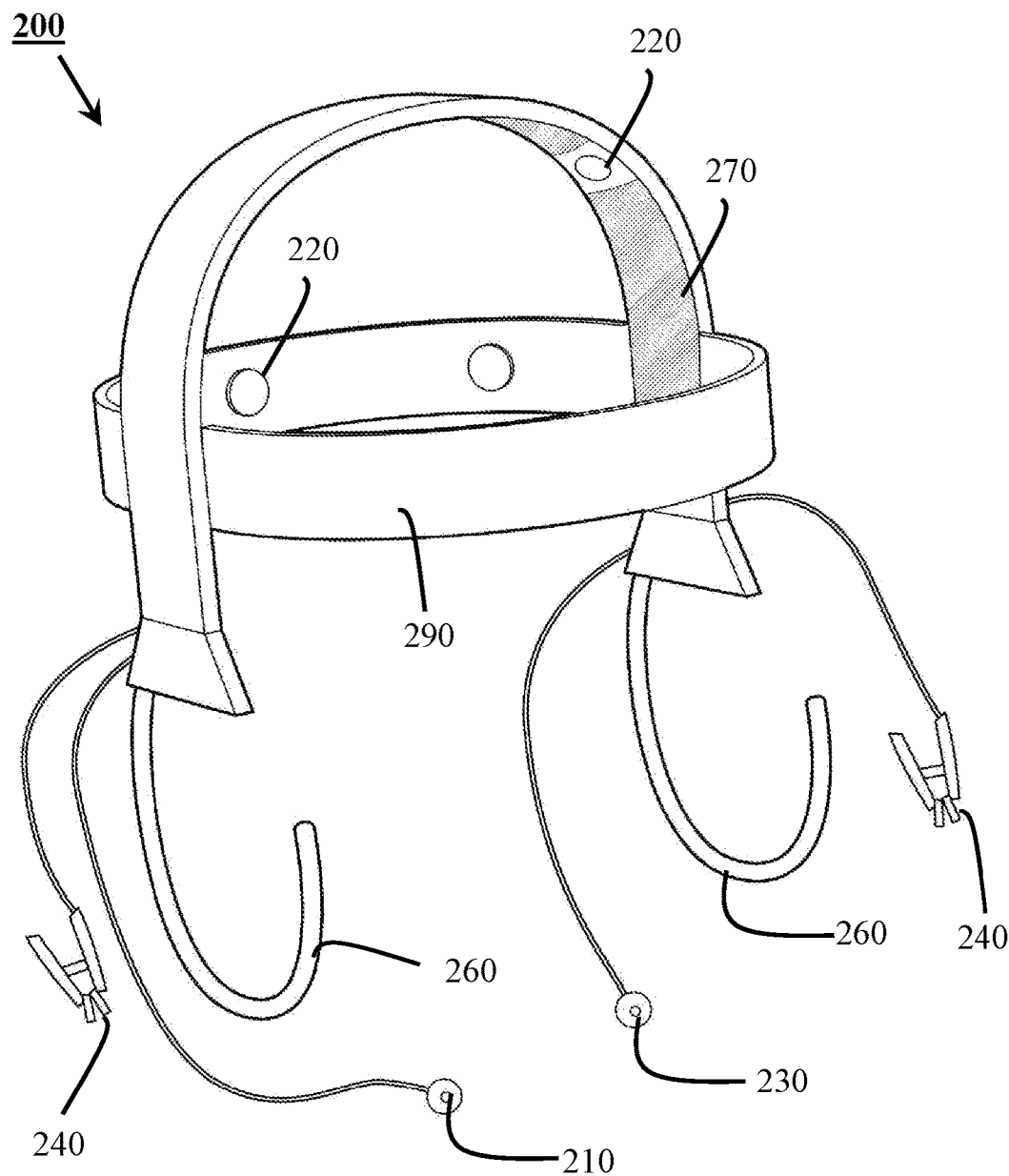
FIG. 6 is a perspective view of a headgear apparatus in accordance with an embodiment of the present invention.

FIG. 6 shows readings of cardiac bioelectrical signals taken using a headgear apparatus in accordance with one embodiment of this invention shown in FIG. 1. Each of AF3, T7, Pz and AF4 denote a recording electrode 30 position at a scalp area of the subject. T8 denotes a recording electrode placed at a chest area of the subject like the second electrode 30 mentioned above. In FIG. 6, sensed cardiac bioelectrical signals are represented in voltage vs. time where voltage represents a relative strength of the signal. As can be seen, the voltage vs time graph representing the cardiac bioelectrical signal for electrode T8 has the highest peak amplitude as it is closest to the source of generation of cardiac electrical activity.

A method of detecting a change in blood flow in a head of a subject comprises measuring a value of a parameter of a cardiac bioelectrical signal at the scalp of the subject relative to a reference cardiac bioelectrical signal.

For example, the parameter of a cardiac bioelectrical signal can be the average peak amplitude of the signal.

Figure 5:
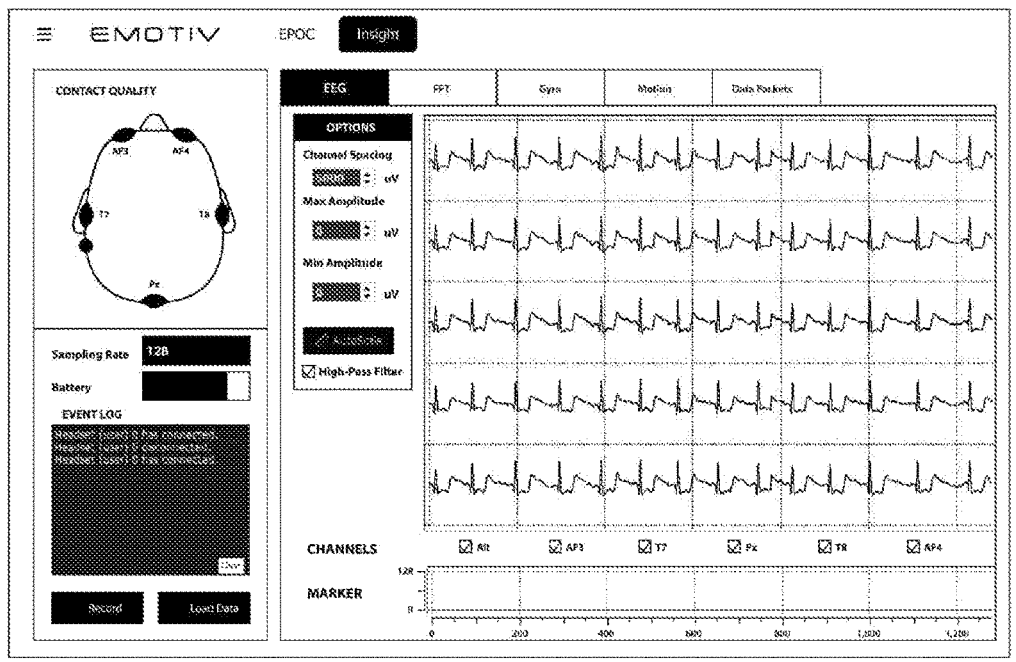
FIG. 5 is a graph of representations of cardiac bioelectrical signals in accordance with an embodiment of the present invention.

The voltage vs time signals shown in FIG. 5 from each of electrodes AF3, T7, Pz and AF4 are examples of cardiac bioelectrical signals taken at a head area of the subject relative to the signal received by a reference electrode located at a chest area of the subject.

In FIG. 5, the parameter is an amplitude of a voltage vs time graph representing a cardiac bioelectrical signal. Advantageously, a cardiac bioelectrical signal has a distinctive, repetitive signature corresponding to the electrical activity required to repeatedly contract the heart over time.

The method further comprises comparing the value of the measured parameter with a predetermined value of the parameter to determine any change in blood flow in the head of the subject.

If the parameter is an average peak amplitude, the predetermined value of the parameter can be the average peak amplitude at the same area where the first electrode is positioned that was recorded when the blood flow in the head of the patient was unimpaired. For example, if the patient has impaired blood flow through the brain compared to when the predetermined value was measured, the measured average peak amplitude value will be lower than the predetermined average peak amplitude value for that patient.

As cardiac bioelectrical activity can be patient-specific, a ratio of the parameter of the measured cardiac bioelectrical signal at the scalp area of the subject, to the parameter of a cardiac bioelectrical signal at the chest area of the subject can be calculated. For example, the peak average amplitude of the cardiac bioelectrical signal recorded by the first electrode relative to the reference electrode can be divided by the average peak amplitude of the cardiac bioelectrical signal recorded by the second electrode relative to the reference electrode. This ratio can be compared to a predetermined ratio, to determine if any change in blood flow to the head has occurred in the subject. For example, the predetermined ratio can be indicative of an average subject with unimpaired blood flow in the head. Alternatively, the predetermined ratio can be indicative of a degree of impaired blood flow in the head of a subject.

This method can be used to monitor a patient continuously to detect any changes in blood flow in the patient's brain over time. For example, during an ischaemic stroke a blood clot is present in a blood vessel in the brain which impairs blood flow within the brain. Using the present method, the peak amplitude of cardiac bioelectrical signal measured at a head area of the subject will be relatively low while the blood clot persists in the blood vessel. If the patient is administered medication to dissolve the clot, the method and headgear apparatus can be used to determine if the clot has been dissolved and whether blood flow in the brain has increased since before the medication was administered.

If the clot dissolves successfully, the peak amplitude of the cardiac bioelectrical signal measured at a head area of the subject will be relatively higher than that measured while the clot was present in the blood vessel. The method and headgear can also be used for various applications where it is beneficial to monitor blood flow in the brain of a subject. For example, the method could be used to monitor conditions that are associated with impaired blood flow in the brain such as delirium or traumatic brain injury.

FIG. 6 illustrates an embodiment of a headgear apparatus for detecting changes in blood flow in a head of a subject.

The headgear apparatus 200 comprises a wearable headgear that can be worn on a user's head. A reference electrode 210 extends from the headgear and can be positioned and applied to a chest area adjacent the heart of the subject. Thus, the reference electrode 210 is locatable on a chest area adjacent a heart of the subject, in use. One or more electrodes 220 are locatable on a scalp area of the subject. One of the electrodes 220 can be a first electrode. Electrodes 220 can be positioned across major cerebral vascular regions to optimise the monitoring of changes in cerebral blood flow.

The headgear apparatus 200 is a wireless, portable EEG headset.

The headgear apparatus includes a second electrode 230 configured to be located at a chest area of the subject, in use, and configured to receive a cardiac bioelectrical signal adjacent the heart, in use.

Each electrode 220 is configured to sense and conduct bioelectrical signals when applied to the body and the headgear apparatus, in use.

Each of the reference electrode 210, one or more electrodes 220 and a second electrode 230 is a scalp electrode operably connected with the EEG headset to sense and receive bioelectrical signals, and convey the bioelectrical signals to the EEG headset.

Each electrode 220 can be a dry or a semi-dry electrode.

The headgear apparatus 200 includes a processing unit (not shown) for receiving the bioelectrical signals from each of the electrodes 210, 220, 230. The processing unit (not shown) is configured to measure a value of a parameter of a cardiac bioelectrical signal recorded at a scalp area of the subject relative to a reference cardiac bioelectrical signal picked up by the reference electrode and to transmit the value of the parameter of the cardiac bioelectrical signal to a remote computer that is configured to determine a change in blood flow in the head of the subject in accordance with the method described above.

For example, the processing unit (not shown) in the headgear apparatus 200 receives bioelectrical signals from each of the electrodes 210, 220, 230 and transmits the cardiac bioelectrical signals to a receiver external to the headgear apparatus. In an embodiment, the processing unit can include a brain-computer interface such as a BCI board that includes a microcontroller for on-board processing of the cardiac bioelectrical signals received from the electrodes. The BCI board can then send the processed cardiac bioelectrical signals to a receiver.

This processed information can be sent to a receiver of a remote computer (not shown). The remote computer (not shown) can use an algorithm for detecting a change in blood flow in the head of a subject in accordance with an embodiment of the method described above. The skilled person will understand that there are multiple ways to implement an embodiment of the method described above.

In the embodiment shown in FIG. 6, the headgear apparatus 200 includes a comb-like portion 270 to clear the forehead of a user wearing the headgear of hair. This will expose the scalp and allow for better electrode contact with the scalp. The headgear apparatus 200 includes a curved piece 280 which extends over the head of the user in use. The headgear apparatus 200 includes an elastic band 290 which extends around the head of the user in use. Electrodes 220 are arranged on the underside of the curved piece 280 and the band. The band 290 is elastic so it can fit securely around heads of different sizes and shapes. The elastic band 290 and curved piece 280 are configured to fit the head of a patient tightly to ensure adequate contact between the electrodes and the scalp of the user to produce accurate results.

Ear hooks 260 are configured to fit around the ears of the user when the headgear apparatus is placed on a user. The ear clip 240 includes a reference electrode 210. The ear clip 240 can be clipped to the ear to use the ear clip as a reference electrode instead of reference electrode 210.

Figure 7:
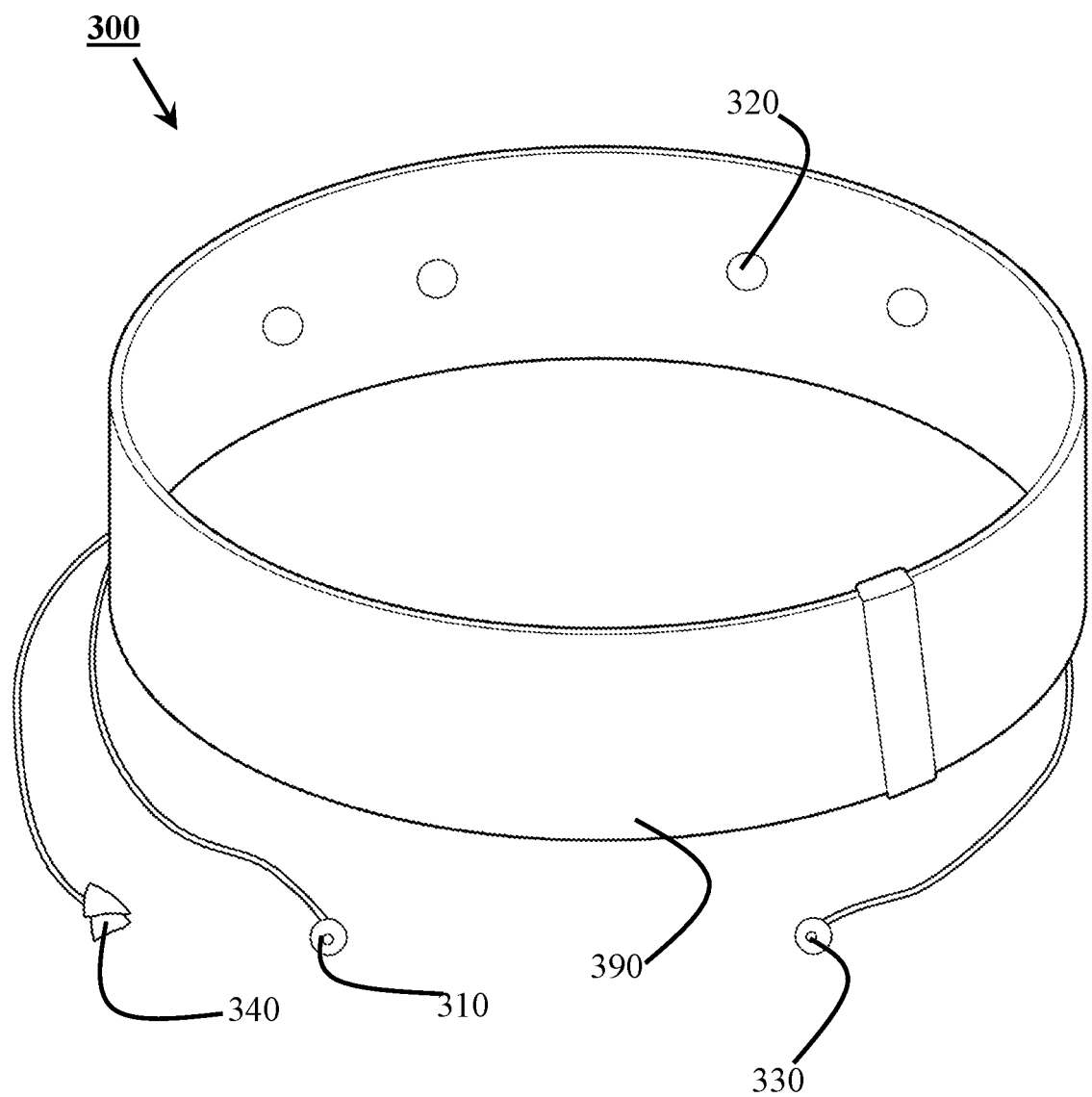
FIG. 7 is a perspective view of a headgear apparatus in accordance with another embodiment of the present invention.

FIG. 7 shows another embodiment of the headgear apparatus. Headgear apparatus 300 has an elastic band 390 which includes electrodes 320. Headgear apparatus 300 has an ear clip 340 which can be used as a reference electrode. Headgear apparatus 300 has a reference electrode 310 that is locatable on a chest area of the user adjacent the heart of the user and an electrode 330 which can be positioned on the chest of a user.

Headgear apparatus 200 and/or 300 can also provide EEG-only functionality by changing the location of the reference electrode 210 from adjacent the heart to another known reference position or by changing the referencing method to those used for acquisition of EEG. In one example, the reference electrode can be placed on the mastoid bone and the first and second electrodes moved to other recording position, for example as identified by the international 10-20 system for EEG electrodes.

In other embodiments the headgear apparatus can include one or more of a variety of sensors such as an accelerometer, temperature sensor, blood oxygenation sensor environmental noise sensor and quantitative EEG.

Parameters measured by the headgear apparatus in addition to cardiac bioelectrical signals at the scalp relative to a reference cardiac bioelectrical signal adjacent the heart of the user, can include:

1). Quantitative EEG (qEEG) measures such as the delta/alpha ratio (DAR).

2). The cardiac and/or an artificially generated electrical signal.

3). Environmental (auditory and visual noise) evoked potentials.

4). Accelerometer. The headset may have an inbuilt accelerometer to monitor a user's head movements in addition to fluid flow changes due to pulsatile perfusion events in the head.

5). Temperature sensor. The Headset may have an infrared temperature sensor to monitor the patients' temperature.

6). Blood oxygenation, via built in oximeter such as a Near infrared (NIR) sensor or Near infrared Spectroscopy (NIRS) or a greenlight pulse oximeter).

The above sensors can be included in the headgear apparatus.

Thus, the headgear apparatus can be used for:

1) Monitoring of electrical signal strength changes at and across cranial positions as a method to infer blood flow changes in the head. This signal can be cardiac and/or an artificially generated signal (eg: EMS or a proprietary signal generator). The cardiac signal could also be used to assess cardiac physiology and monitor heart rate.

2) monitoring environmental stimuli affecting the brain, specifically light stimuli and auditory stimuli with reference to the relevant cortex evoked potentials as a means to monitor brain function changes and cortex sensitivities in real time.

3) monitoring brain function in real-time using the aforementioned methods in combination with standard EEG measures, particularly the delta:alpha signal ratio changes with time and with potential to detect and monitor perfusion changes, seizures, delirium and intra-cranial pressure.

4) monitoring the relative signal strengths across the electrodes could be used to map regions of ischemia, changes due to treatment, vasospasm/delayed cerebral ischemia, long term injury and potential changes during recovery.

5) monitoring head movements (via accelerometer) whether due to gross patient movements or fluid flow changes from pulsatile perfusion events in the head. Temperature and blood oxygenation (NIR/greenlight pulse oximeter) will also be monitored.

It is envisaged that in embodiments other than the illustrated embodiments, wireless electrodes can be used.

The headgear apparatus 200, 300 can be used for continuous or semi-continuous monitoring blood flow in the brain. The headgear apparatus 200, 300 can be a low voltage-low power wireless electronic device such that is poses a low electrical safety risk.

Embodiments of the headgear apparatus and method could be used in a number of other applications including paramedic assessment, emergency medicine, delirium, traumatic brain injury, seizures, monitoring of intra-cranial pressure and neurorehabilitation.

The described method of detecting changes in blood flow in a head of a subject will allow a physician or nurse to quantitatively monitor stroke patients between CT/MRI scans. It will allow stroke treatment to be monitored in real-time providing information about treatment outcome which will help guide the next steps in management of the patient. If treatment is unsuccessful, the device will be able to alert clinicians to this faster than current methods, allowing patients to be given secondary treatment if required.

The method and headgear apparatus for detecting changes in blood flow in the head of a subject could also be used to detect vasospasm/delayed cerebral ischemia in patients that have experienced subarachnoid haemorrhage. These patients can be continuously monitored these patients to detect the onset of vasospasm or decompression illness (DCI). Transcranial doppler ultrasound is currently used to detect vasospasm however this is not a continuous method and it is sometimes not very accurate. A new fast accurate method to detect vasospasm/DCI will allow patients to be given treatment faster than possible with current methods of detection. This could prevent irreversible damage that could otherwise be caused by vasospasm/DCI.

The method and headgear apparatus for detecting changes in blood flow in the head of a subject could also be used to monitor seizures, delirium, traumatic brain injury, intracranial pressure and neuro-rehabilitation.

In another embodiment, the headgear apparatus may be part of a 'smart helmet' that could be used to monitor wakefulness in professions where hard hats are typically used.

Monitoring of cardiac bioelectrical signal at the head of the patient could also be used to assess cardiac physiology and monitor heart rate. Any changes in cardiac signal during exercise can inform the status of the cardiac physiology of the patient.

Experimental Report

An experiment was conducted to test the following hypothesis:

The heart generates the largest electrical signal in the body and blood is one of the most electrically conductive components in the body, hence providing a major pathway for electrical signal propagation. It was hypothesized that reduced cerebral blood flow will reduce this propagation and thus reduce the amplitude of the hearts electrical signal recorded across the scalp, compared to the amplitude of the hearts electrical signal recorded at the chest. It was hypothesized that increased cerebral blood flow will increase this propagation and thus increase the amplitude of the hearts electrical signal recorded across the scalp, compared to the amplitude of the hearts electrical signal recorded at the chest. This method could be useful for monitoring of patients with stroke, sleep apnoea, delirium, traumatic brain injury or other disorders associated with impaired cerebral blood flow.

Figure 2:
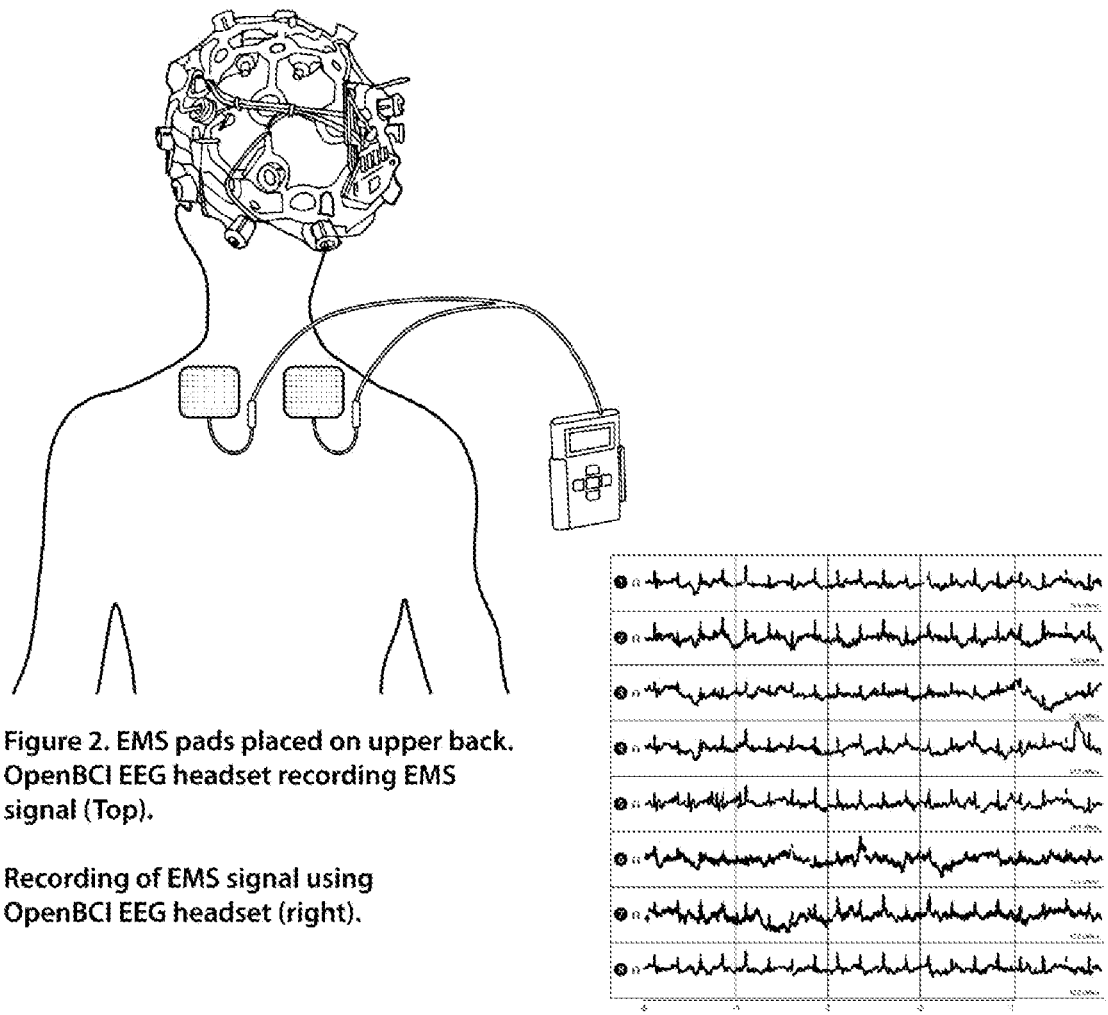
FIG. 2 shows the setup and results of an experiment conducted using an artificially generated EMS signal.

By re-positioning the reference electrode of an EMOTIV Insight EEG headset to a left chest position, the cardiac bioelectrical signal across EEG scalp electrodes was detected. The scalp electrode T8 was repositioned to a right chest position to record the cardiac bioelectrical signal across the chest as shown in FIG. 1. Applicant investigated how anaerobic exercise-induced reductions in CBF (via push-ups) impact the amplitude of the cardiac bioelectrical signal and an EMS signal (using an OpenBCI EEG headset) across the scalp (FIG. 2). Applicant also investigated how this impacted the scalp cardiac bioelectrical signal amplitude as a percentage of the chest cardiac bioelectrical signal amplitude.

Results: 1 minute after anaerobic exercise, both the cardiac biosignal amplitude and EMS-induced signal amplitude decreased (P<0.05) in scalp electrodes. Signal amplitude returned back to baseline after 5 minutes. (FIG. 3). The scalp cardiac biosignal amplitude as a percentage of the chest cardiac biosignal amplitude also decreased 1 minute after anaerobic exercise. It then increased towards baseline after 4 minutes (FIG. 4).

The decreases in cardiac biosignal amplitude and EMS signal amplitude across the scalp and the scalp cardiac biosignal amplitude as a percentage of the chest cardiac biosignal amplitude that were observed, may be caused by a reduction in CBF (cerebral blood flow) induced by anaerobic exercise. The EMS signal is a control stimulus as it is independent of cardiac physiology. These findings provide preliminary evidence that decreased CBF may be detected by decreases in extra-cerebral electrical signals recorded across the scalp.

Experiment with Control

The method described above are based on a hypothesis that changes in blood flow alter the propagation of electrical signals. The hypothesis was tested using an artificially generated electrical signal (generated by an electrical muscle stimulation (EMS) device). The EMS signal acts as a control measure as its generation is independent of the user's physiology.

EMS pads were placed on the upper back. Stimulation was set to a constant frequency. This generated electrical signal was recorded using an EEG headset as shown in FIG. 2.

The recording of the EMS signal using an OpenBCI EEG headset measuring electrical activity at the scalp showed that the signature of the artificially generated electrical signal was present in the electrical activity of the head measured near the scalp of the subject.

Embodiments

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the above description of example embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description of Specific Embodiments are hereby expressly incorporated into this Detailed Description of Specific Embodiments, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

Specific Details

In the description provided herein, numerous specific details are set forth. However, it is understood that embodiments of the invention may be practiced without these specific details. In other instances, well-known methods, structures and techniques have not been shown in detail in order not to obscure an understanding of this description.

COMPRISING AND INCLUDING

In the claims which follow and in the preceding description of the invention, except where the context requires otherwise due to express language or necessary implication, the word "comprise" or variations such as "comprises" or "comprising" are used in an inclusive sense, i.e. to specify the presence of the stated features but not to preclude the presence or addition of further features in various embodiments of the invention.

Any one of the terms: including or which includes or that includes as used herein is also an open term that also means including at least the elements/features that follow the term, but not excluding others. Thus, including is synonymous with and means comprising.

SCOPE OF INVENTION

Thus, while there has been described what are believed to be the described embodiments of the invention, those skilled in the art will recognize that other and further modifications may be made thereto without departing from the spirit of the invention, and it is intended to claim all such changes and modifications as fall within the scope of the invention. For example, any formulas given above are merely representative of procedures that may be used. Functionality may be added or deleted from the block diagrams and operations may be interchanged among functional blocks. Steps may be added or deleted to methods described within the scope of the present invention.

Although the invention has been described with reference to specific examples, it will be appreciated by those skilled in the art that the invention may be embodied in many other forms.

The invention claimed is:

1. A method of detecting changes in blood flow in a head of a subject comprising:
    measuring a value of a parameter of a cardiac bioelectrical signal at a scalp area of the subject relative to a reference cardiac bioelectrical signal;
    comparing the value of the measured parameter with a predetermined value of the parameter to determine any change in blood flow in the head of the subject;
    measuring a value of the parameter of a cardiac bioelectrical signal at a chest area of the subject relative to the reference cardiac bioelectrical signal; and
    calculating a ratio of the parameter of the measured cardiac bioelectrical signal at the scalp area of the subject to the parameter of a cardiac bioelectrical signal at the chest area of the subject.

2. The method of claim 1, further comprising:
    comparing the ratio to a predetermined ratio that is indicative of a state of unimpaired blood flow.

3. The method of claim 1, further comprising:
    comparing the ratio to a predetermined ratio that is indicative of a state of impaired blood flow.

4. The method of claim 1, wherein the reference cardiac bioelectrical signal is an ECG measurement taken at a chest area adjacent the heart of the subject or across a chest area of the subject.

5. The method of claim 1, wherein the parameter is an average peak amplitude of a voltage vs. time graph that is indicative of the measured cardiac bioelectrical signal.

6. The method of claim 1, wherein the reference cardiac bioelectrical signal is received by a reference electrode located adjacent a heart of the subject.

7. A system for detecting changes in blood flow in a head of a subject, comprising:
    a reference electrode locatable at a chest area of the subject;
    a first electrode locatable on a scalp area of the subject, the first electrode configured to receive a bioelectrical signal relative to the reference electrode;
    a second electrode locatable at a chest area of the subject, in use, and configured to receive a cardiac bioelectrical signal adjacent the heart relative to the reference electrode;
    a headgear connected to each of the reference electrode and the first electrode, the headgear comprising:
    a processing unit configured to measure a value of a parameter of a cardiac bioelectrical signal received at the scalp area of the subject relative to a reference cardiac bioelectrical signal received at the chest area of the subject and transmit the value of the parameter of that cardiac bioelectrical signal to a computer that is configured to determine a change in blood flow in the head of the subject.

8. The system of claim 7, wherein the processing unit is a brain-computer interface.

9. The system of claim 7, further comprising a receiver to receive the transmitted cardiac bioelectrical signal, wherein the receiver is a wireless receiver.

10. The system of claim 7, wherein one or more of the reference electrode, the first electrode and the second electrode is a wireless electrode.

* * * * *